US 9,859,086 B2

(12) United States Patent
Kakutani et al.

(10) Patent No.: US 9,859,086 B2
(45) Date of Patent: Jan. 2, 2018

(54) ION SOURCE

(71) Applicant: Kabushiki Kaisha Toshiba, Tokyo (JP)

(72) Inventors: Akiko Kakutani, Yokohama (JP);
Kiyoshi Hashimoto, Yokohama (JP);
Kiyokazu Sato, Tokyo (JP); Akihiro Osanai, Yokohama (JP); Takeshi Yoshiyuki, Yokohama (JP); Tsutomu Kurusu, Tokyo (JP)

(73) Assignee: KABUSHIKI KAISHA TOSHIBA, Tokyo (JP)

( * ) Notice: Subject to any disclaimer, the term of this patent is extended or adjusted under 35 U.S.C. 154(b) by 0 days.

(21) Appl. No.: 13/781,913

(22) Filed: Mar. 1, 2013

(65) Prior Publication Data

US 2013/0228699 A1  Sep. 5, 2013

(30) Foreign Application Priority Data

Mar. 2, 2012 (JP) ................. 2012-046416

(51) Int. Cl.
*H01J 27/24* (2006.01)
*H01J 27/02* (2006.01)
(Continued)

(52) U.S. Cl.
CPC ............ *H01J 27/24* (2013.01); *H01J 27/024* (2013.01); *A61N 2005/1085* (2013.01); *H01J 37/08* (2013.01)

(58) Field of Classification Search
CPC .......... H01J 37/08; H01J 27/024; H01J 49/10; H01J 2237/08; H01J 27/24; A61N 2005/1088
(Continued)

(56) References Cited

U.S. PATENT DOCUMENTS 3,406,349 A * 10/1968 Swain ..................... H01J 27/02
250/423 P
3,593,018 A * 7/1971 Cohen ........................... 250/288
(Continued)

FOREIGN PATENT DOCUMENTS

CN    1933092 A    3/2007
CN    102290315 A    12/2011
(Continued)

OTHER PUBLICATIONS

Office Action dated Apr. 15, 2014, in Japanese Application No. 2012-046416, filed Mar. 2, 2012 (with English-language translation).

(Continued)

*Primary Examiner* — Wyatt Stoffa
(74) *Attorney, Agent, or Firm* — Oblon, McClelland, Maier & Neustadt, L.L.P.

(57) ABSTRACT

According to one embodiment, there is provided an ion source. The ion source includes a vacuum-exhausted vacuum chamber, a target which is set in the vacuum chamber and generates a plurality of valences of ions by irradiation of a laser beam, an acceleration electrode which is applied with voltage in order to accelerate the ions generated by the target, and an intermediate electrode which is provided between the target and the acceleration electrode and is applied with reverse voltage of the voltage applied to the acceleration electrode.

3 Claims, 2 Drawing Sheets

(51) Int. Cl.
*A61N 5/10* (2006.01)
*H01J 37/08* (2006.01)

(58) Field of Classification Search
USPC .............................................. 250/281, 423 R
See application file for complete search history.

(56) References Cited

U.S. PATENT DOCUMENTS

| | | | | |
|---|---|---|---|---|
| 4,649,278 | A * | 3/1987 | Chutjian et al. | 250/423 R |
| 5,245,192 | A * | 9/1993 | Houseman | 250/423 R |
| 5,569,917 | A * | 10/1996 | Buttrill et al. | 250/292 |
| 5,614,711 | A * | 3/1997 | Li et al. | 250/287 |
| 5,742,049 | A * | 4/1998 | Holle et al. | 250/282 |
| 6,033,973 | A * | 3/2000 | Takemura | 438/514 |
| 6,140,656 | A | 10/2000 | Fujii | |
| 6,744,225 | B2 * | 6/2004 | Okamura | H05H 9/00 |
| | | | | 250/423 R |
| 7,196,337 | B2 * | 3/2007 | Mikolas | 250/423 R |
| 8,872,127 | B2 * | 10/2014 | Okamura | A61N 5/10 |
| | | | | 250/423 R |
| 2002/0166960 | A1 * | 11/2002 | Pronko | B01D 59/44 |
| | | | | 250/282 |
| 2002/0180365 | A1 * | 12/2002 | Okamura | H05H 9/00 |
| | | | | 315/111.81 |
| 2003/0030013 | A1 * | 2/2003 | Yamashita | H01J 37/3171 |
| | | | | 250/492.21 |
| 2003/0150984 | A1 * | 8/2003 | Guevremont et al. | 250/281 |
| 2003/0201389 | A1 * | 10/2003 | Hartley | 250/287 |
| 2004/0036032 | A1 * | 2/2004 | Leung et al. | 250/423 R |
| 2004/0238753 | A1 * | 12/2004 | Mikolas | H01J 37/08 |
| | | | | 250/396 R |
| 2004/0238755 | A1 * | 12/2004 | Lee | H01J 49/147 |
| | | | | 250/423 R |
| 2006/0273252 | A1 * | 12/2006 | Hayden et al. | 250/282 |
| 2007/0075240 | A1 * | 4/2007 | Hieke | H01J 49/04 |
| | | | | 250/282 |
| 2009/0200485 | A1 * | 8/2009 | Kolodney et al. | 250/424 |
| 2009/0224700 | A1 * | 9/2009 | Chen et al. | 315/505 |
| 2010/0090103 | A1 * | 4/2010 | Mueller et al. | 250/287 |
| 2010/0264328 | A1 * | 10/2010 | Biloiu et al. | 250/424 |
| 2010/0301199 | A1 * | 12/2010 | Chen et al. | 250/282 |
| 2011/0101237 | A1 * | 5/2011 | Jung | G21K 5/04 |
| | | | | 250/423 R |
| 2012/0025072 | A1 * | 2/2012 | Toyoda et al. | 250/287 |
| 2012/0211668 | A1 * | 8/2012 | Okamura | A61N 5/10 |
| | | | | 250/282 |
| 2014/0225000 | A1 * | 8/2014 | Kakutani | H01J 49/164 |
| | | | | 250/423 P |
| 2015/0115169 | A1 * | 4/2015 | Hieke | H01J 49/04 |
| | | | | 250/398 |

FOREIGN PATENT DOCUMENTS

| | | |
|---|---|---|
| JP | 11-111185 A | 4/1999 |
| JP | 2000-146914 A | 5/2000 |
| JP | 3713524 | 9/2005 |
| JP | 2007-057432 | 3/2007 |
| JP | 2009-37764 | 2/2009 |
| RU | 2 096 856 C1 | 11/1997 |
| WO | WO 2010109907 A1 * | 9/2010 |

OTHER PUBLICATIONS

Combined Office Action and Search Report dated Mar. 27, 2015 in Chinese Patent Application No. 201310064976.0 (with English language translation).

* cited by examiner

ION SOURCE

CROSS-REFERENCE TO RELATED APPLICATIONS

This application is based upon and claims the benefit of priority from Japanese Patent Application No. 2012-046416, filed Mar. 2, 2012, the entire contents of which are incorporated herein by reference.

FIELD

Embodiments described herein relate generally to an ion source that generates an ion by irradiation of a laser beam.

BACKGROUND

In general, as a method of generating an ion in an ion source, for example, a method of acquiring the ion by causing discharge in gas has been known. In this case, a microwave or an electron beam may be used in order to cause the discharge.

Meanwhile, a technology that generates ions by using a laser is present. By an ion source that generates the ions by using the laser, a laser beam is collected and irradiated onto a solid target, an element contained in the target is vaporized and ionized by energy of the laser beam to generate plasmas, the ions contained in the plasmas are transported as the plasmas are, and the ions are accelerated while extracting an ion beam.

According to the ion source, the ions can be generated by irradiating the laser to the solid target and it is advantageous in generation of the multi-charged ion.

However, ions in every charge state coexist in the ions generated in the ion source as described above.

In this case, for example, a high-frequency acceleration linear accelerator is used at a rear end of the ion source to selectively transport only a necessary ion of a valence, but in an ion source by itself, ions of valences which are unnecessary cannot be removed.

DETAILED DESCRIPTION

Hereinafter, embodiments of the invention will be described with reference to the accompanying drawings. According to one embodiment, in general, there is provided an ion source, including: a vacuum-exhausted vacuum chamber; a target which is set in the vacuum chamber and generates a plurality of valences of ions by irradiation of a laser beam; an acceleration electrode which is applied with voltage in order to accelerate the ions generated by the target; and an intermediate electrode which is provided between the target and the acceleration electrode and is applied with reverse voltage of the voltage applied to the acceleration electrode.

First Embodiment

Figure 1:
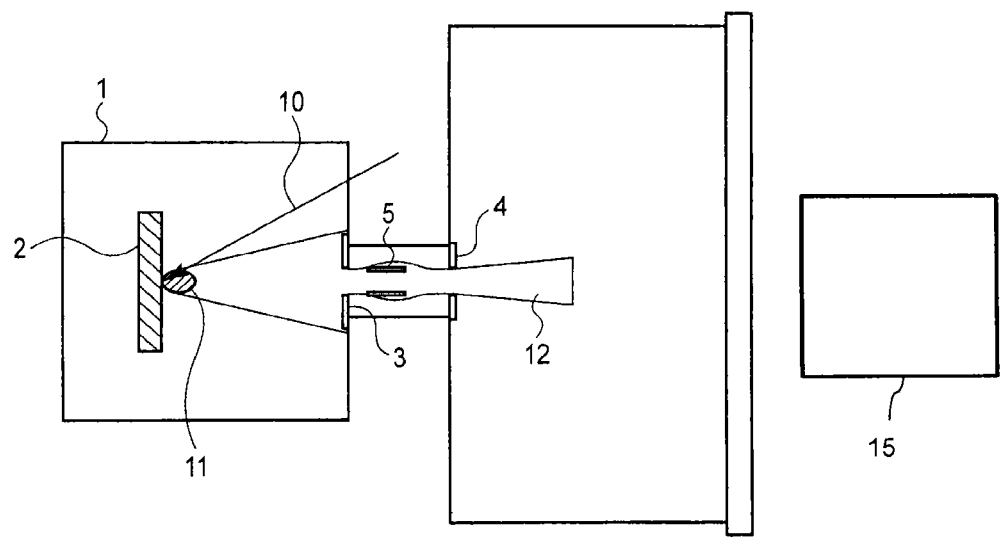
FIG. 1 is a schematic cross-sectional view of a configuration of an ion source according to a first embodiment of the invention.

First, an ion source according to a first embodiment of the invention will be described with reference to FIG. 1. FIG. 1 schematically illustrates a configuration of an ion source according to the embodiment. The ion source according to the embodiment is, for example, a laser ion source that collects and irradiates a laser beam onto a target and vaporizes and ionizes an element contained in the target by energy of the laser beam to generate ions.

As illustrated in FIG. 1, the ion source includes a vacuum chamber 1, a target 2, a collimator 3, an acceleration electrode 4, and an intermediate electrode 5.

The vacuum chamber 1 is made of, for example, stainless steel and the target 2 is set in the vacuum chamber 1. Further, the vacuum chamber 1 is vacuum-exhausted by an exhaust system (not illustrated).

A laser beam 10 is collected and irradiated onto the target 2 in the vacuum chamber 1 to generate a plurality of valences of ions. In detail, for example, the laser beam 10 collected by using a focusing lens (not illustrated) provided in the vacuum chamber 1 is irradiated to the target 2, and as a result, a laser ablation plasma (hereinafter, simply referred to as a plasma) 11 is generated. The plasma 11 contains a multi-charged ion of a target material as a target in the ion source. Further, the target 2 is, for example, a carbon based plate-like member.

The collimator 3 is installed between the target 2 and the acceleration electrode 4 and excludes unnecessary plasmas from the plasmas 11 generated by irradiating the laser beam 10 to the target 2.

The acceleration electrode 4 is applied with voltage to accelerate the ion contained in the plasma 11 transported via the collimator 3. As a result, an electric field for accelerating and focusing the ion contained in the plasma 11 is generated and the ion is accelerated, in the acceleration electrode 4. Further, the ion accelerated by the acceleration electrode 4 is finally emitted from the ion source as an ion 12.

The intermediate electrode 5 is installed between the collimator 3 and the acceleration electrode 4 and is applied with reverse voltage of the voltage applied to the acceleration electrode 4.

Subsequently, an operation of the ion source according to the embodiment will be described. Further, the ion generated from the ion source according to the embodiment is an ion caused by the ion contained in the target 2 and the plurality of valences of ions coexists. As the target 2, for example, a carbon target, and the like are contained.

First, the laser beam 10 collected by using the focusing lens is irradiated to the target 2 set in the vacuum chamber 1. In this case, the plasma 11 is generated in the target 2. In the case where the target 2 is the carbon target, for example, ions of $C^{6+}$ to $C^{1+}$ coexist in the plasma 11. Further, the plasma 11 from which the unnecessary plasma is removed by the collimator 3 is incident in the intermediate electrode 5.

Herein, the reverse voltage of the voltage applied to the acceleration electrode 4 is applied to the intermediate electrode 5 as described above, and the voltage value is set as an optimal value depending on the multi-charged ion of the target material, which is the target in the ion source, to prevent an ion, which is low in speed, such as, for example, a cluster ion, and the like among the plurality of valences of ions contained in the plasma 11 from passing through the intermediate electrode 5. As a result, unnecessary ions may be avoided from being introduced into a downstream part.

Further, a shape and voltage of the intermediate electrode 5 are optimized to focusing of the ion to control trajectory of the ion and improve a yield of the ion.

The ion, which passes through the intermediate electrode 5, is accelerated by the acceleration electrode 4. Further, the ion accelerated by the acceleration electrode 4 is emitted from the ion source as the ion 12 to be transported to the outside (for example, a linear accelerator 15, and the like) of the ion source.

Further, the plurality of valences of ions contained in the plasma 11 is different from each other in velocity. As a result, the plurality of valences of respective ions contained in the plasma 11 is different from each other in, for example, observation time in the intermediate electrode 5. By using the feature, pulse driving voltage is applied to the intermediate electrode 5 (that is, the intermediate electrode 5 is pulse-driven) to allow only an ion of a valence, which is a target in the ion source, among the plurality of valences of ions (that is, the plurality of valences of ions generated in the target 2) contained in the plasma 11 to pass through the intermediate electrode 5 (that is, transported to the acceleration electrode 4), for example, at a timing depending on a velocity of the multi-charged ion (that is, the ion of the valence which is the target in the ion source) of the target material which is the target in the ion source.

Figure 2:
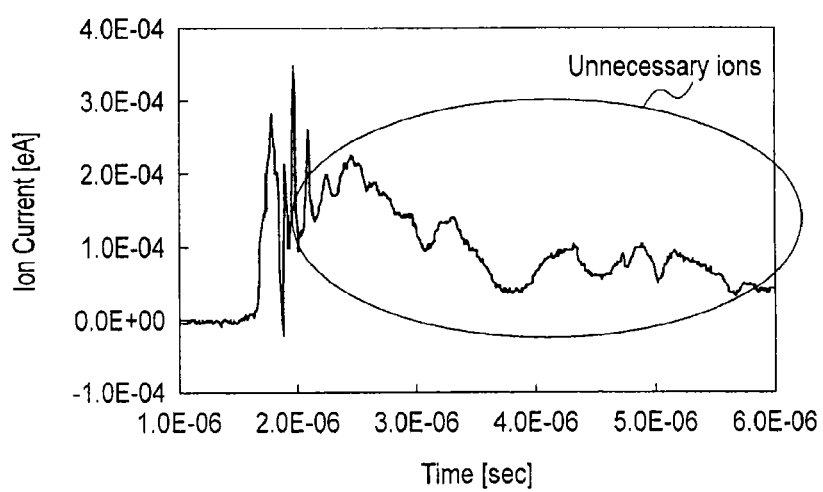
FIG. 2 is a characteristic diagram illustrating ions which are incident in an intermediate electrode 5.

Herein, FIG. 2 illustrates, for example, the ion incident in the intermediate electrode 5. As illustrated in FIG. 2, the ion incident in the intermediate electrode 5 includes the multi-charged ion of the target material which is the target in the ion source and the unnecessary ion.

Figure 3:
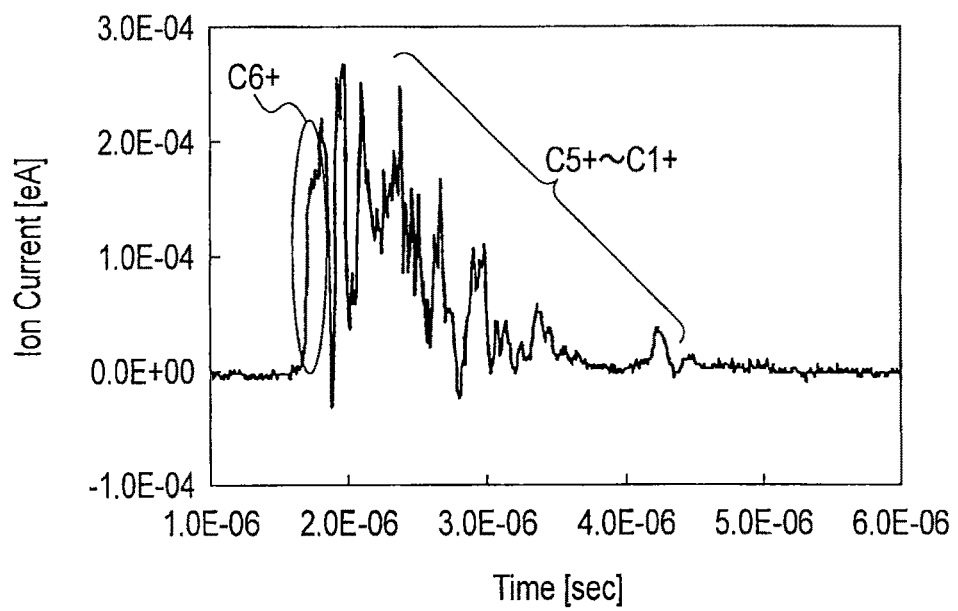
FIG. 3 is a characteristic diagram illustrating ions in the case where a positive electric field is applied to the intermediate electrode 5.

FIG. 3 illustrates an ion in the case where reverse voltage (for example, a positive electric field) of the voltage applied to the acceleration electrode 4 is applied to the intermediate electrode 5.

As illustrated in FIG. 3, the reverse voltage of the voltage applied to the acceleration electrode 4 is applied to the intermediate electrode 5 to remove the unnecessary ion illustrated in FIG. 2.

Further, as illustrated in FIG. 3, in the case where the target 2 is the carbon target, for example, $C^{6+}$ to $C^{1+}$ coexist in the ion observed in the intermediate electrode 5.

Since $C^{6+}$ to $C^{1+}$ are different from each other in velocity as described above, $C^{6+}$ to $C^{1+}$ are different from each other in time observed in the intermediate electrode 5, as illustrated in FIG. 3.

In this case, when the ion of the valence, which is the target in the ion source, is set as $C^{6+}$, the intermediate electrode 5 is pulse-driven to lower voltage only while $C^{6+}$ passes through the intermediate electrode 5 and voltage is applied to prevent the ion from passing through the intermediate electrode 5 during the rest thereof to enable only $C^{6+}$ to pass through the intermediate electrode 5.

Further, herein, $C^{6+}$ is the ion of the valence which is the target in the ion source, but the intermediate electrode 5 is pulse-driven at a timing depending on a velocity of an ion other than $C^{6+}$, which is the target, to enable only the ion to pass through the intermediate electrode 5.

In the embodiment as described above, by the configuration which includes the vacuum-exhausted vacuum chamber 1, the target 2 set in the vacuum chamber 1 and generating the plurality of valences of ions by the irradiation of the laser beam, the acceleration electrode 4 applied with voltage in order to accelerate the ion generated by the target 2, and the intermediate electrode 5 provided between the target 2 and the acceleration electrode 4 and applied with the reverse voltage of the voltage applied to the acceleration electrode 4, the ion, which is low in speed, such as the cluster ion, and the like are unable to pass through the intermediate electrode 5. Therefore, the unnecessary ion may be excluded.

Further, in the embodiment, the configuration in which the pulse driving voltage is applied to the intermediate electrode 5 at a timing depending on a velocity of an ion of a predetermined valence, which is a target in the ion source, enables only the ion of the valence, which is the target, to be transported to the acceleration electrode 4.

In addition, in the embodiment, the pulse driving voltage may be applied to the acceleration electrode 4 (the acceleration electrode 4 is pulse-driven) so as to accelerate only the ion of the valence, which is the target, at the timing depending on the velocity of the ion of the valence which is the target in the ion source.

Second Embodiment

Figure 4:
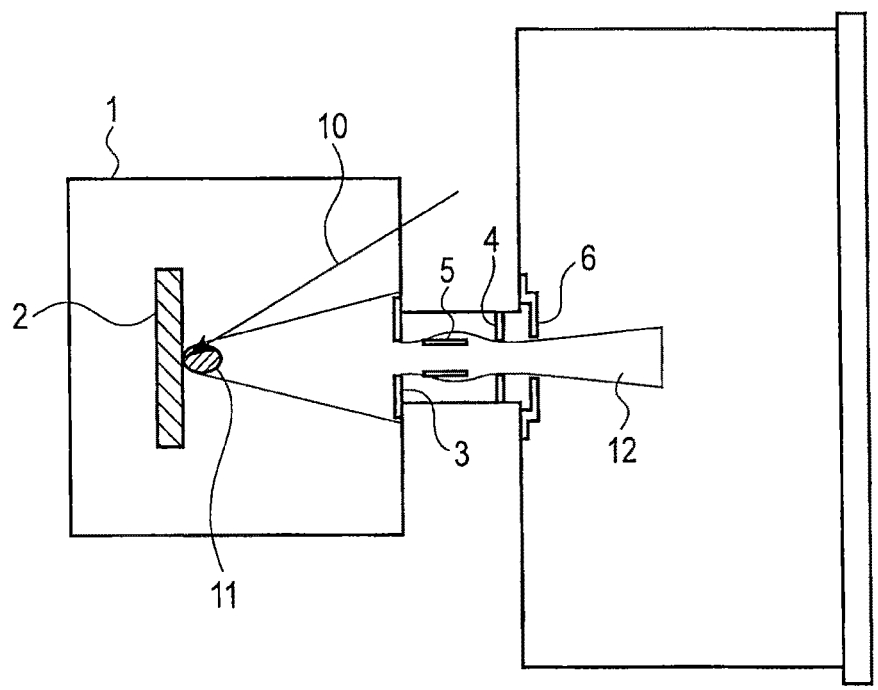
FIG. 4 is a schematic cross-sectional view of a configuration of an ion source according to a second embodiment of the invention.

Subsequently, an ion source according to a second embodiment of the invention will be described with reference to FIG. 4. FIG. 4 schematically illustrates a configuration of an ion source according to an embodiment. Further, in FIG. 4, the same reference numerals refer to the same components as FIG. 1 and a detailed description thereof will be omitted.

As illustrated in FIG. 4, the ion source according to the embodiment is different from that of the first embodiment, in that an auxiliary electrode 6 is provided downstream of an acceleration electrode 4.

In the embodiment, pulse driving voltage is applied to the auxiliary electrode 6 to transport an ion of a predetermined valence (that is, the ion of the valence which is the target in the ion source) among the ions accelerated by the acceleration electrode 4 (that is, the auxiliary electrode 6 is pulse-driven). As a result, only the ion of the valence, which is the target, may be transported to the downstream part.

Further, a pulse width of pulse driving in the auxiliary electrode 6 may be increased by adjusting a position where the auxiliary electrode 6 is installed and voltage applied to the auxiliary electrode 6. As a result, coexistence rate of ions other than the ion of the valence, which is the target, may be lowered.

In the embodiment as described above, by a configuration in which the auxiliary electrode 6 installed downstream of the acceleration electrode 4 is provided and the pulse driving voltage is applied to the auxiliary electrode 6 to transport the ion of the predetermined valence among the ions accelerated by the acceleration electrode 4, only the ion of the valence which is the target in the ion source is transported.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A method of using an ion source connected with a linear accelerator as a downstream apparatus, the ion source, including: a vacuum-exhausted vacuum chamber, and a carbon target which is set in the vacuum chamber and generates a plurality of valences of carbon ions by irradiation of a laser beam, the plurality of valences of ions including a multi-charged ion of a target material to be used in the ion source, the method comprising:

applying, to an acceleration electrode, a voltage to accelerate the carbon ions generated by the carbon target, the acceleration electrode generating an electric field for accelerating and focusing the carbon ions; and applying, to an intermediate electrode which is provided between the carbon target and the acceleration electrode, a reverse voltage of the voltage applied to the acceleration electrode having a value depending on the multi-charged carbon ion of the target material among a plurality of valences of carbon ions generated from the carbon target, the intermediate electrode focusing the multi-charged carbon ion of the target material, wherein the applying to the intermediate electrode and the reverse voltage comprises applying to the intermediate electrode a pulse driving voltage depending on a predetermined velocity of the multi-charged carbon ion of the target material among the plurality of valences of carbon ions which has been generated by the target and which have different velocities, only while the multi-charged carbon ion of the target material passes through the intermediate electrode to transport only the multi-charged carbon ion of the target material to the acceleration electrode, and wherein the multi-charged carbon ion of the target material, which has been passed through the intermediate electrode and accelerated by the acceleration electrode, is emitted from the ion source and transported to the linear accelerator.

2. The method according to claim 1, further comprising:
applying to an auxiliary electrode which is installed downstream of the acceleration electrode, a pulse driving voltage to transport the multi-charged carbon ion of the target material, among the carbon ions accelerated by the acceleration electrode, downstream of the auxiliary electrode.

3. The method according to claim 1, further comprising:
excluding, by a collimator between the target and the acceleration electrode, unnecessary plasmas from plasmas which are generated from the target.

* * * * *